(12) United States Patent
Gong et al.

(10) Patent No.: US 12,085,508 B2
(45) Date of Patent: Sep. 10, 2024

(54) SYNCHRONOUS FLUORESCENCE DETECTOR FOR OBSERVING INTERFACE CONCENTRATION OF FLUORESCENT POLLUTANTS AND APPLICATION METHOD

(71) Applicant: SOUTH CHINA UNIVERSITY OF TECHNOLOGY, Guangzhou (CN)

(72) Inventors: Xiangjun Gong, Guangzhou (CN); Wenzhang Tian, Guangzhou (CN); Yongping Zeng, Guangzhou (CN); Lianjun Bao, Guangzhou (CN); Guangzhao Zhang, Guangzhou (CN); Xiao Liang, Guangzhou (CN); Xiawen Qiu, Guangzhou (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 305 days.

(21) Appl. No.: 17/749,162

(22) Filed: May 20, 2022

(65) Prior Publication Data
US 2022/0276166 A1     Sep. 1, 2022

Related U.S. Application Data

(63) Continuation of application No. PCT/CN2020/127680, filed on Nov. 10, 2020.

(30) Foreign Application Priority Data

Nov. 20, 2019  (CN) .......................... 201911143148.X

(51) Int. Cl.
*G01N 21/64*   (2006.01)
*G01N 13/00*   (2006.01)
*G01N 33/18*   (2006.01)

(52) U.S. Cl.
CPC ........... *G01N 21/645* (2013.01); *G01N 13/00* (2013.01); *G01N 33/1826* (2013.01);
(Continued)

(58) Field of Classification Search
CPC ......... G01N 21/645; G01N 2021/6471; G01N 2021/6478; G01N 2021/6484; G01N 2021/6463; G01N 21/6428
See application file for complete search history.

(56) References Cited

U.S. PATENT DOCUMENTS

| | | | |
|---|---|---|---|
| 2004/0200723 A1 | 10/2004 | Sakai et al. | |
| 2010/0068821 A1* | 3/2010 | St. Germain | ...... G01N 33/1826 436/140 |

FOREIGN PATENT DOCUMENTS

| | | |
|---|---|---|
| CN | 207571030 | 7/2018 |
| CN | 109387592 | 2/2019 |

(Continued)

OTHER PUBLICATIONS

"International Search Report (Form PCT/ISA/210) of PCT/CN2020/127680", mailed on Feb. 8, 2021, with English translation thereof, pp. 1-4.

*Primary Examiner* — David P Porta
*Assistant Examiner* — Meenakshi S Sahu
(74) *Attorney, Agent, or Firm* — JCIPRNET

(57) ABSTRACT

Provided are a synchronous fluorescence detector for observing the interface concentration of fluorescent pollutants and application method. The detector comprises a first electric displacement platform, a quartz cuvette, an excitation light path, a collection light path and a second electric displacement platform. The application method comprises the following steps: first exciting fluorescent pollutants by utilizing UV light with specific wavelengths to emit fluorescent light; then collecting fluorescence signals emitted by the excited fluorescent pollutants to the greatest extent by (Continued)

utilizing an UV anti-reflection convex lens combination; and finally, processing the fluorescent signals acquired by a photomultiplier by utilizing a difference method to determine a precise light intensity of a thin layer which is moved at a specific spacing by utilizing the electric displacement platforms so as to determine fugacity distribution of the fluorescent pollutants in the microlayer near an interface.

18 Claims, 8 Drawing Sheets

(52) U.S. Cl.
CPC .................. *G01N 2013/003* (2013.01); *G01N 2021/6471* (2013.01); *G01N 2021/6478* (2013.01); *G01N 2021/6484* (2013.01)

(56) References Cited

FOREIGN PATENT DOCUMENTS

| | | |
|---|---|---|
| CN | 110108552 | 8/2019 |
| CN | 110793887 | 2/2020 |
| CN | 212008213 | 11/2020 |

\* cited by examiner

SYNCHRONOUS FLUORESCENCE DETECTOR FOR OBSERVING INTERFACE CONCENTRATION OF FLUORESCENT POLLUTANTS AND APPLICATION METHOD

CROSS-REFERENCE TO RELATED APPLICATION

This application is a continuation of international application of PCT application serial no. PCT/CN2020/127680 filed on Nov. 10, 2020, which claims the priority benefit of China application no. 201911143148.X filed on Nov. 20, 2019. The entirety of each of the above mentioned patent applications is hereby incorporated by reference herein and made a part of this specification.

TECHNICAL FIELD

The present invention relates to a detector and application method for measuring diffusion concentration distribution of environmental pollutants near the air-water interface and the sediment-water interface, particularly to a method for quantitatively analyzing diffusion concentration distribution of fluorescent pollutants in the microlayer near the air-water interface and the sediment-water interface by means of a synchronous fluorescence detector.

RELATED ART

Intercompartmental transfer of organic pollutants in the sediment-water interface, the soil-atmosphere interface and the air-water interface forms a basic frame of global migration. Migration rules of pollutants propelled by free activity difference in the three interfaces are not only similar but also slightly different.

The air-water interface exchange is an environmental process of exchange with the maximum area. One of challenges to quantify the exchange flux of the organic pollutants in the air-water interface is to determine its concentration or fugacity distribution near the interface. Fugacity trend that controls the air-water interface exchange is usually distributed in the microlayer between two phases, and its thickness is several millimeters to centimeters or smaller. Therefore, if it fails to measure the fugacity distribution of the organic pollutants passing through the microlayer effectively to estimate the exchange flux across the air-water interface, a large deviation will be generated.

Passive sampling method is often used to monitor actual water environmental pollutants, which enrich samples by using extraction media with high distribution coefficients without additional power, so that it is suitable for field environmental monitoring. Existing passive sampling methods for pore water pollutants of sediments mainly include a novel in-situ solid phase micro-extraction technology and a low-density polyethylene film extraction technology.

For the passive sampling method with respect to pollutant monitoring, the acquired samples cannot reflect concentration change of the pollutants in the microlayer near the air-water interface as the minimum spacing between adjacent two extraction and acquisition units is 0.17 cm.

SUMMARY OF INVENTION

Technical Problem

Technical Solution for the Technical Problem

Technical Solution

In order to solve the above-mentioned problems, the present invention provides a synchronous fluorescence detector for observing the interface concentration of fluorescent pollutants and application method. In order to overcome defects and shortcomings of existing mainstream technology, the present invention is mainly intended to provide a method capable of quantitatively analyzing diffusion concentration distribution of fluorescent pollutants in the microlayer near the air-water interface and the sediment-water interface. The method provides effective information to research fugacity distribution of organic pollutants near the air-water interface and the sediment-water interface in the true environment.

A technical solution of the present invention used for solving the technical problems is as follows:

A synchronous fluorescence detector for observing the interface concentration of fluorescent pollutants includes a first electric displacement platform, a quartz cuvette, an excitation light path, a collection light path and a second electric displacement platform, wherein the excitation light path includes a high-power xenon lamp optical fiber light source, a short wavelength pass filter, an UV collimator, a first UV anti-reflection convex lens and a second UV anti-reflection convex lens; the collection light source includes a UV anti-reflection convex lens, a fourth UV anti-reflection convex lens, a long wavelength pass filter and a photomultiplier;

the excitation light path is integrated on the first electric displacement platform; the collection light path is integrated on the second electric displacement platform; the excitation light path and the collection light path are respectively close to the quartz cuvette; one side of the short wavelength pass filter is provided with the high-power xenon lamp optical fiber light source and another side of the short wavelength pass filter is provided with the UV collimator; another side of the UV collimator is provided with the first UV anti-reflection convex lens and the second UV anti-reflection convex lens;

in the excitation light path, divergent light emitted by the high-power xenon lamp optical fiber light source passes through the short wavelength pass filter and forms a divergent beam in a narrow wave band, the beam passes through the UV collimator to obtain an approximately parallel beam, the approximately parallel beam passes through the first UV anti-reflection convex lens and the second UV anti-reflection convex lens to form a thinner approximately parallel beam as incident light, and the incident light enters the quartz cuvette to excite a fluorescent pollutant to emit fluorescence;

in the collection light path, a fluorescence signal emitted by the excited fluorescent pollutant passes through the third UV anti-reflection convex lens, the fourth UV anti-reflection convex lens and the long wavelength pass filter in sequence and is collected by the photomultiplier.

Further, in the excitation light path, the distance between the first UV anti-reflection convex lens and the second UV anti-reflection convex lens have to satisfy a corresponding relation between focal lengths of the two lenses.

Further, in the excitation light path, a distance between the second UV anti-reflection convex lens and the quartz cuvette is about 1-2 cm; and in the collection light path, a distance between the third UV anti-reflection convex lens and the quartz cuvette is about 1-2 cm.

Further, in the excitation light path, centers of the short wavelength pass filter, the UV collimator, the first UV anti-reflection convex lens and the second UV anti-reflection convex lens are on a same horizontal line; and in the collection light path, centers of the third UV anti-reflection convex lens, the fourth UV anti-reflection convex lens, the long wavelength pass filter and the photomultiplier are on a same horizontal line.

Further, an angle between the excitation light path and the collection light path can be 0 degree, 90 degrees or 180 degrees.

Further, a wavelength of the high-power xenon lamp optical fiber light source is as follows: 250 nm<$\lambda$<1000 nm; a filter range of the short wavelength pass filter is as follows: 300 nm<$\lambda$<350 nm; a ratio of the focal length of the first UV anti-reflection convex lens to that of the second UV anti-reflection convex lens is 1:4; a filter range of the long wavelength pass filter is as follows: 350 nm<$\lambda$<500 nm; a distance between the photomultiplier and the long wavelength pass filter is about 0.5-1 cm; and the minimum displacements of the first electric displacement platform and the second electric displacement platform moving longitudinally are 5 μm.

Further, as an improvement of the technical solution of the present invention, in the excitation light path, a lens combination formed by the first UV anti-reflection convex lens and the second UV anti-reflection convex lens can be replaced by different types of UV collimators, thereby improving the degree of parallelism of incident light.

Further, as an improvement of the technical solution of the present invention, in the excitation light path, a columnar collecting lens can be used in front of the UV collimator to control width and thickness of a beam;

Further, as an improvement of the technical solution of the present invention, in a whole light path system, the light filter can be replaced by a monochromator to emit and collect UV light with specific wavelength.

Further, as an improvement of the technical solution of the present invention, in the collection light path, a lens combination formed by the two UV anti-reflection convex lenses with different focal lengths can be replaced by an UV objective lens with a greater NA value, so as to collect fluorescent signals emitted by the fluorescent pollutants to the greatest extent.

Further, as an improvement of the technical solution of the present invention, the whole fluorescent signal acquisition process can be controlled by LabVIEW to be realized automatically.

An application method of the synchronous fluorescence detector for observing the interface concentration of fluorescent pollutants includes the following specific steps:

S1. turning on a power supply of the high-power xenon lamp optical fiber light source to preheat for about 10 min;

S2. connecting communications between the first electric displacement platform (1) and a computer and between the second displacement platform and the computer, and setting overload parameters "velocity=2.5 mm/s, acceleration=0.5 mm/s$^2$" to protect the displacement platforms;

S3. connecting a communication between a counter of the photomultiplier and the computer, setting required parameters, and setting a single measurement time to be 2 s;

S4. controlling the first electric displacement platform and the second displacement platform (12) to move simultaneously by LabVIEW after preheating is completed, and acquiring data by using the photomultiplier, and repeating the step S4 in such a manner till an experiment is completed; and S5. processing the data acquired by the photomultiplier via a Python software and Excel.

Further, the data processing method uses a difference method and a successive differential method.

Further, when the overall length of beam scanning is smaller than the width of a beam, the difference method can be represented in a simplified manner as follows:

It is assumed that $I_i$ is a light intensity acquired when the photomultiplier moves to a position where a beam starting point height is z; $\Delta I_i$ represents a fluorescence intensity in a layer of z→z+iΔz.

$$\Delta I_i = I_i - I_{i-1}$$

The fluorescence intensity in a very thin layer can be roughly acquired by means of small spacing scanning and the difference method.

Further, when the precise width w of a parallel beam can be measured precisely, the successive differential method can be represented in a simplified manner as follows:

It is assumed that $I_i$ is a light intensity acquired when the photomultiplier moves to a position where the beam starting point height is z; $\Delta I_i$ represents the fluorescence intensity in a layer of z→z+iΔz. It is set that k=w/Δz, w is the precise with of the beam, and Δz is a moving spacing of the displacement platform.

$$\Delta I_i = (I_i - I_{i-1}) + \Delta I_{i-k}$$

The fluorescence intensity (shown in FIG. 5 and FIG. 6) in the very thin layer can be precisely acquired by means of the successive differential method.

Beneficial Effects of the Present Invention

The present invention has the beneficial effects:

Compared with the prior art, the present invention, the technical solution of the present invention has the following beneficial effects:

The minimum displacement measured at one time can reach 5 μm, so that diffused concentration distribution of the fluorescent pollutants in the microlayer near the interface can be measured. The fluorescence signals emitted by the fluorescent pollutants can be acquired in a same position for many times. The measuring progress can be controlled in real time by LabVIEW, and a tester can set the control time and progress of the acquired signals according to a time resolution required according to an actual condition. The present invention contributes to improvement of the time resolution in indoor simulated true environment sampling greatly, thereby providing effective data for researching fugacity distribution of the fluorescent pollutants in the microlayer near the interface in the indoor simulated true environment.

Figure 1:
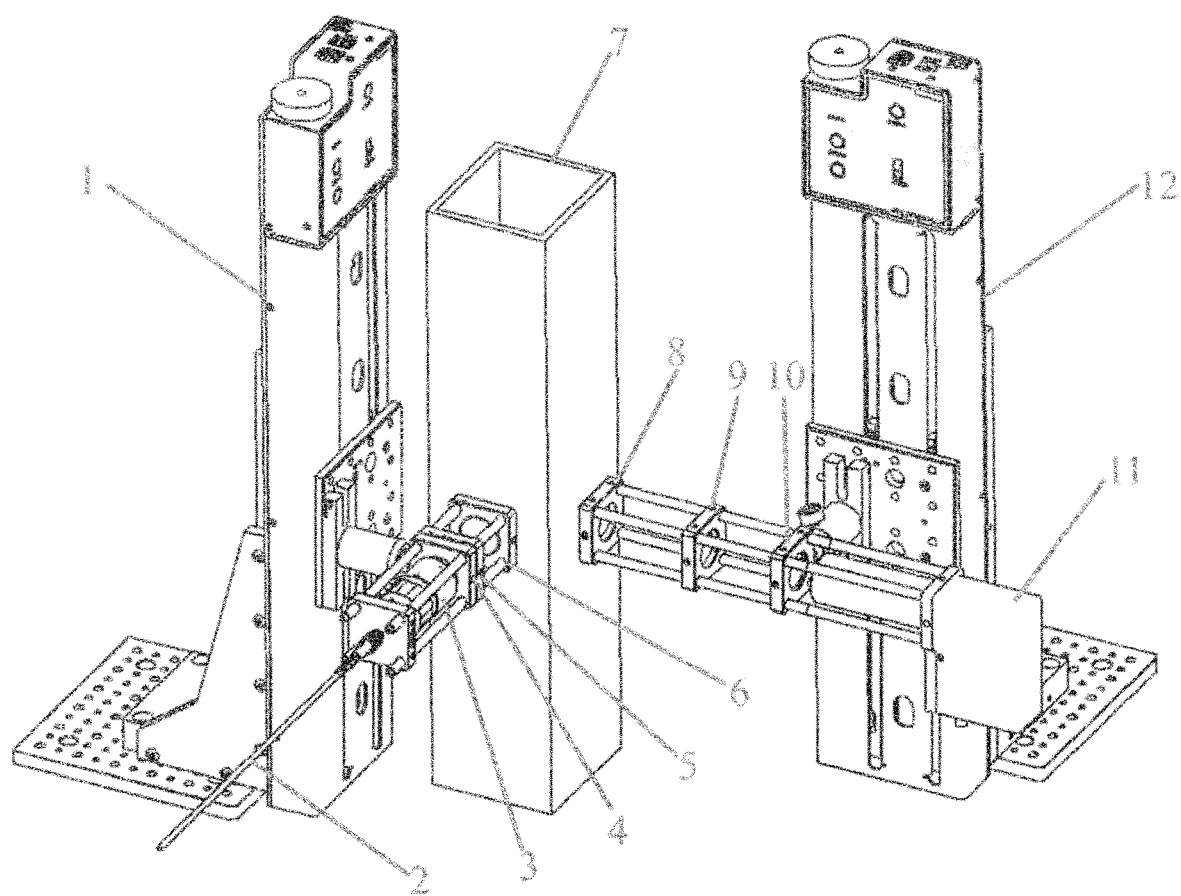
FIG. 1 is a schematic diagram of a synchronous fluorescence detector of an embodiment of the present invention.
Figure 2:
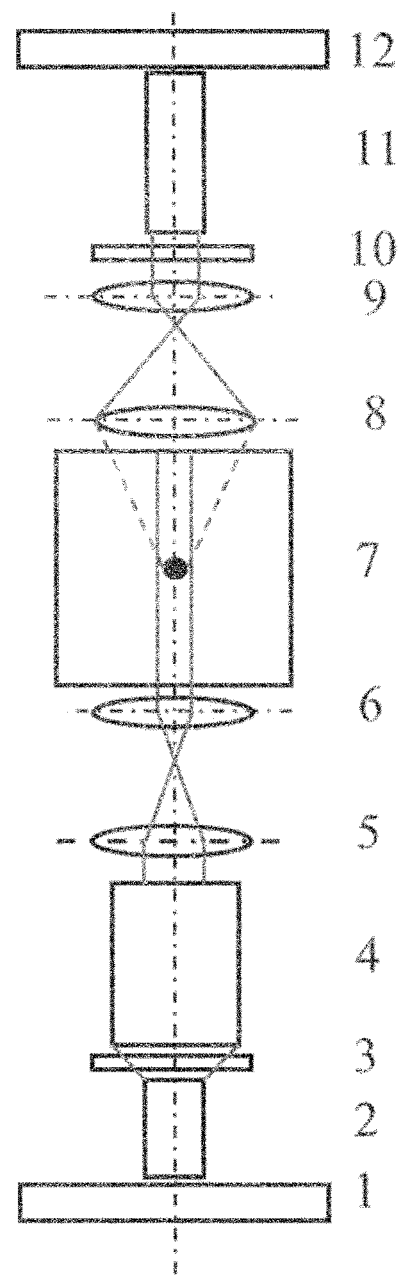
FIG. 2 is a schematic diagram of a 0-degree light path of a synchronous fluorescence detector of an embodiment of the present invention.
Figure 3:
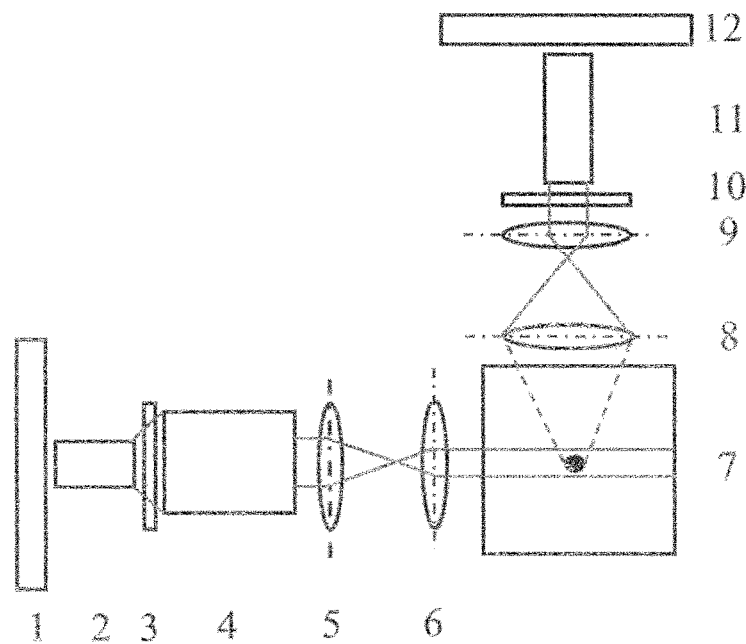
FIG. 3 is a schematic diagram of a 90-degree light path of a synchronous fluorescence detector of an embodiment of the present invention.
Figure 4:
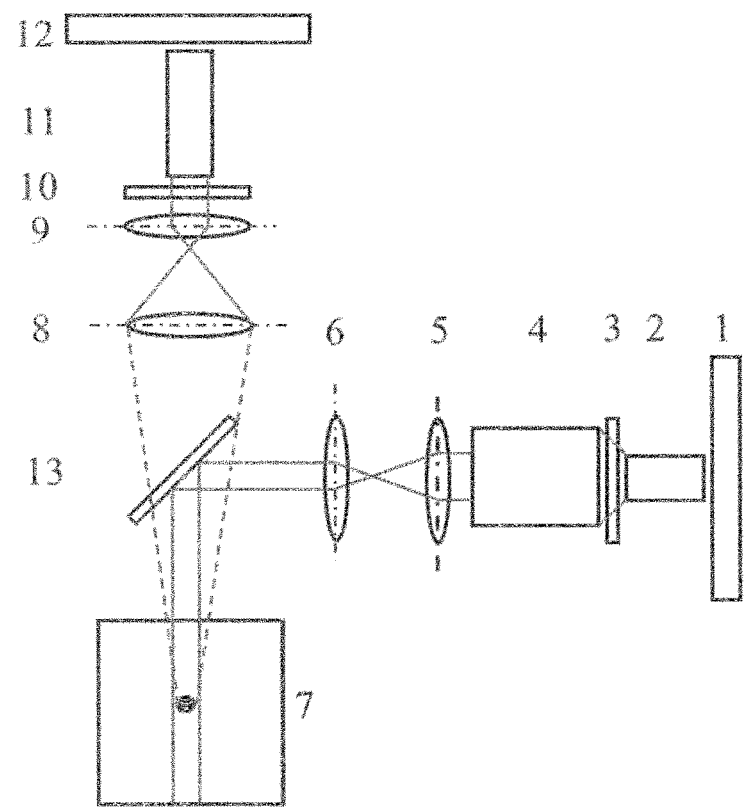
FIG. 4 is a schematic diagram of a 180-degree light path of a synchronous fluorescence detector of an embodiment of the present invention.

First electric displacement platform 1, high-power xenon lamp optical fiber light source 2, short wavelength pass filter 3, UV collimator 4, first UV collimator convex lens 5, second UV collimator convex lens 6, quartz cuvette 7, third UV collimator convex lens 8, fourth UV collimator convex lens 9, long wavelength pass filter 10, photomultiplier 11 and second electric displacement platform 12.

DESCRIPTION OF EMBODIMENTS

Further detailed description of the present invention will be made below in combination with embodiments and drawings, but it is to be noted that the embodiments do not limit the protection scope claimed by the present invention.

A synchronous fluorescence detector for pollutants concentration near the interface in the embodiment includes a first electric displacement platform 1, a quartz cuvette 7, an excitation light path, a collection light path and a second electric displacement platform 12, wherein the excitation light path includes a high-power xenon lamp optical fiber light source 2, a short wavelength pass filter 3, an UV collimator 4, a first UV anti-reflection convex lens 5 and a second UV anti-reflection convex lens 6; the collection light source includes a third UV anti-reflection convex lens 8, a fourth UV anti-reflection convex lens 9, a long wavelength pass filter 10 and a photomultiplier 11; the excitation light path is arranged on the first electric displacement platform 1; the collection light path is arranged on the second electric displacement platform 12; the excitation light path and the collection light path are respectively close to the quartz cuvette 7; one side of the short wavelength pass filter 3 is provided with the high-power xenon lamp optical fiber light source 2 and another side of the short wavelength pass filter 3 is provided with the UV collimator 4; another side of the UV collimator 4 is provided with the first UV anti-reflection convex lens 5 and the second UV anti-reflection convex lens 6; in the excitation light path, divergent light emitted by the high-power xenon lamp optical fiber light source 2 passes through the short wavelength pass filter 3 and forms a divergent beam in a narrow wave band, the beam passes through the UV collimator 4 to obtain an approximately parallel beam, the approximately parallel beam passes through the first UV anti-reflection convex lens 5 and the second UV anti-reflection convex lens 6 to form a thinner approximately parallel beam as incident light, and the incident light enters the quartz cuvette 7 to excite a fluorescent pollutant to emit fluorescent light; and in the collection light path, a fluorescence signal emitted by the excited fluorescent pollutant passes through the third UV anti-reflection convex lens 8, the fourth UV anti-reflection convex lens 9 and the long wavelength pass filter 10 in sequence and is collected by the photomultiplier 11. In the excitation light path, a distance between the first UV anti-reflection convex lens 5 and the second UV anti-reflection convex lens 6 has to satisfy a corresponding relation of a focal length between the two lenses.

In the embodiment, in the excitation light path, a distance between the second UV anti-reflection convex lens 6 and the quartz cuvette 7 is about 1 cm, a distance between the first UV anti-reflection convex lens 5 and the second UV anti-reflection convex lens 6 is 10 cm, a distance between the UV collimator 4 and the first UV anti-reflection convex lens 5 is 1 cm, a distance between the short wavelength pass filter 3 and the UV collimator 4 is 0.5 cm, and a distance between the high-power xenon lamp optical fiber light source 2 and the short wavelength pass filter 3 is 0.5 cm; and in the collection light path, a distance between the third UV anti-reflection convex lens 8 and the quartz cuvette 7 is about 1 cm, a distance between the third UV anti-reflection convex lens 8 and the fourth UV anti-reflection convex lens 9 is 5 cm, a distance between the fourth UV anti-reflection convex lens 9 and the long wavelength pass filter 10 is 0.5 cm, and a distance between the long wavelength pass filter 10 and the photomultiplier 11 is 0.5 cm.

In the excitation light path, centers of the short wavelength pass filter 3, the UV collimator 4, the first UV anti-reflection convex lens 5 and the second UV anti-reflection convex lens 6 are on a same horizontal line; and in the collection light path, centers of the third UV anti-reflection convex lens 8, the fourth UV anti-reflection convex lens 9, the long wavelength pass filter 10 and the photomultiplier 11 are on a same horizontal line. Further, a wavelength of the high-power xenon lamp optical fiber light source 2 is as follows: 250 nm<$\lambda$<1000 nm; a filter range of the short wavelength pass filter 3 is as follows: 300 nm<$\lambda$<350 nm; a ratio of the focal length of the first UV anti-reflection convex lens 5 to that of the second UV anti-reflection convex lens 6 is 1:4; a filter range of the long wavelength pass filter 10 is as follows: 350 nm<$\lambda$<500 nm; a distance between the photomultiplier 11 and the long wavelength pass filter is about 0.5 cm; and the minimum displacements of the first electric displacement platform 1 and the second electric displacement platform 12 moving longitudinally are 5 μm.

As a preferred embodiment of the present invention, collection results of the embodiment use a 90-degree light path. In the excitation light path, the UV collimator and the UV anti-reflection plano-convex lenses with focal lengths of f=80 mm and f=20 mm form a cage light path; and in the collection light path, a long focal length lens combination is replaced by short focal length anti-reflection plano-convex lenses with focal lengths of f=16 mm and f=20 mm and large NA values so as to improve the collection efficiency of the fluorescence signals. The displacements platforms in the embodiment are LTS300/M displacement platforms which are purchased from Thorlabs Optical Electronic TECHNOLOGY(Shanghai) Co., Ltd.

Embodiment 1

A synchronous fluorescence detector for observing interface concentration of fluorescent pollutant measures the fluorescence intensity distribution of pyrene molecules with 1 ppm pyrene solution in the microlayer near an interface, including the following specific steps:

S1: a ppm pyrene solution is prepared and the pyrene solution is left still for three days in a low light condition of a lab at 21-25° C.;

S2: a power supply of the high-power xenon lamp optical fiber light source (2) is turned on to preheat for about 10 min;

S3: communications between the first electric displacement platform (1) and a computer and between the second displacement platform (12) and the computer are connected, and overload parameters "velocity=2.5 mm/s, acceleration=0.5 mm/s$^2$" are set;

S4: a communication between a counter of the photomultiplier (11) and the computer is connected, and a single measurement time is set to be 2 s, the 1 ppm pyrene solution is selected to be a sample here;

S5: the first electric displacement platform (1) and the second displacement platform (12) are controlled to move simultaneously by LabVIEW after preheating is completed, and data is acquired by using the photomultiplier (11), and the step S5 is repeated in such a manner till an experiment is completed; and S6: the data acquired by the photomultiplier (11) is processed via a Python software and Excel, the data being calculated as follows (part of data is taken as an example):

It is assumed that $I_i$ is a light intensity acquired when the photomultiplier moves to a position where a beam starting point height is z; $\Delta I_i$ represents a fluorescence intensity in a layer of $z \rightarrow z+i\Delta z$.

$$\Delta I_i = I_i - I_{i-1}$$

Figure 5:
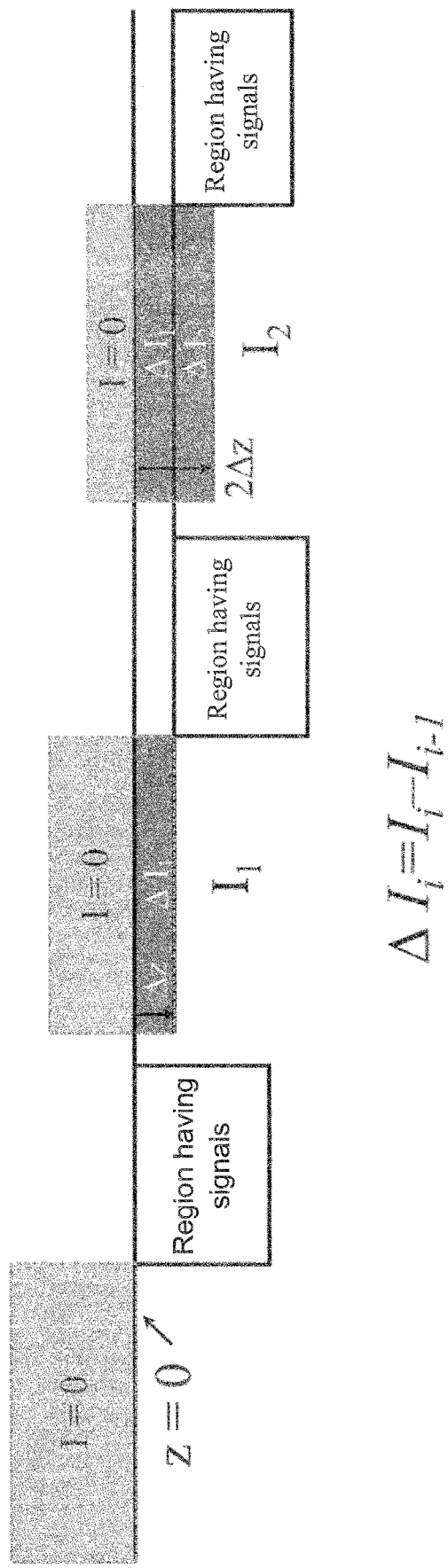
FIG. 5 is a schematic diagram of a difference method in data processing of an embodiment of the present invention.
Figure 6:
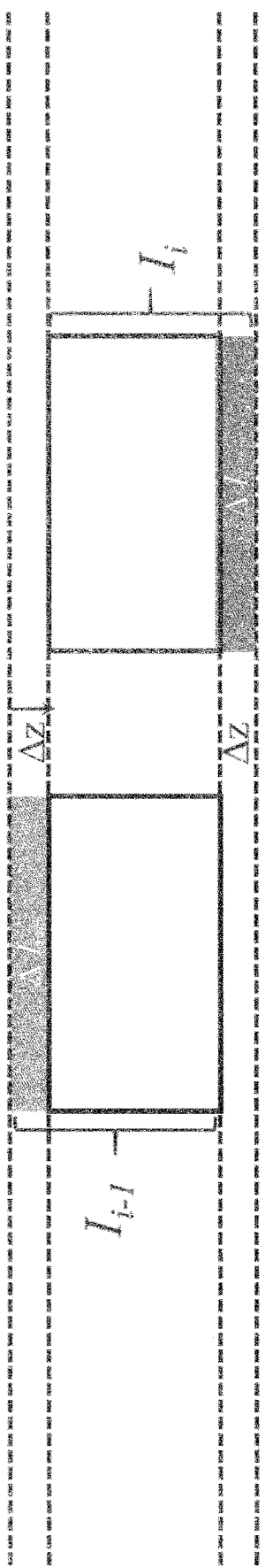
FIG. 6 is a schematic diagram of a successive differential method in data processing of an embodiment of the present invention.
Figure 7:
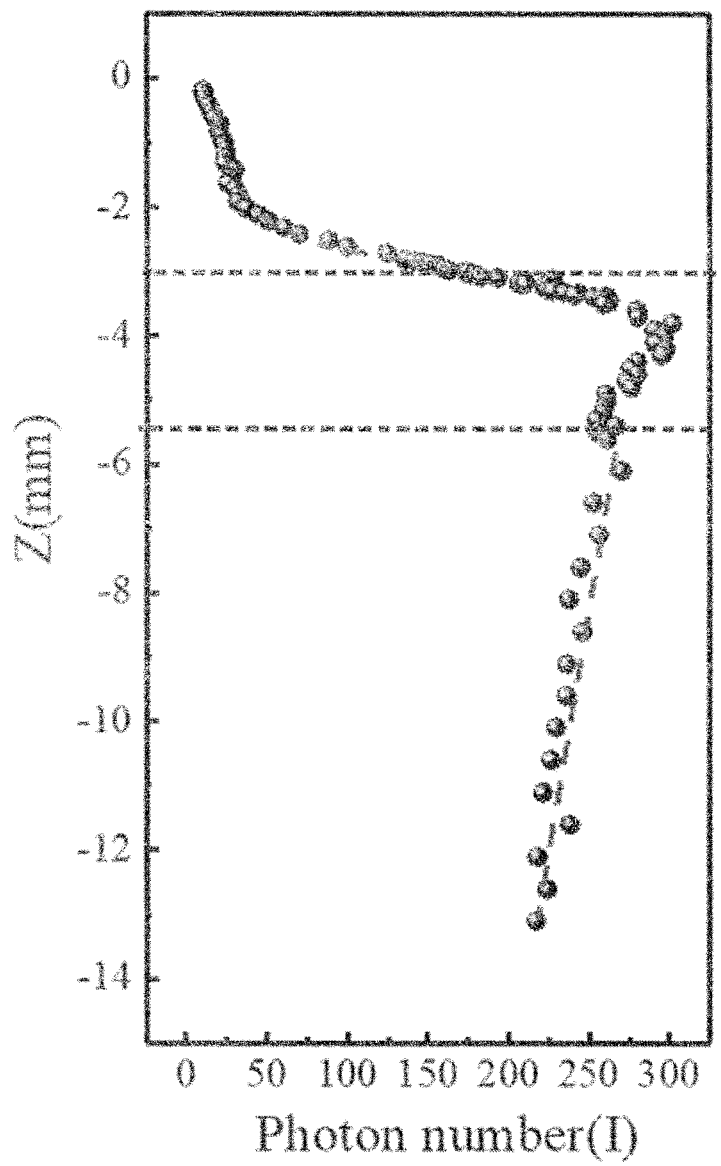
FIG. 7 is a distribution curve of a total light intensity in an illumination beam to z in an embodiment of the present invention.
Figure 8:
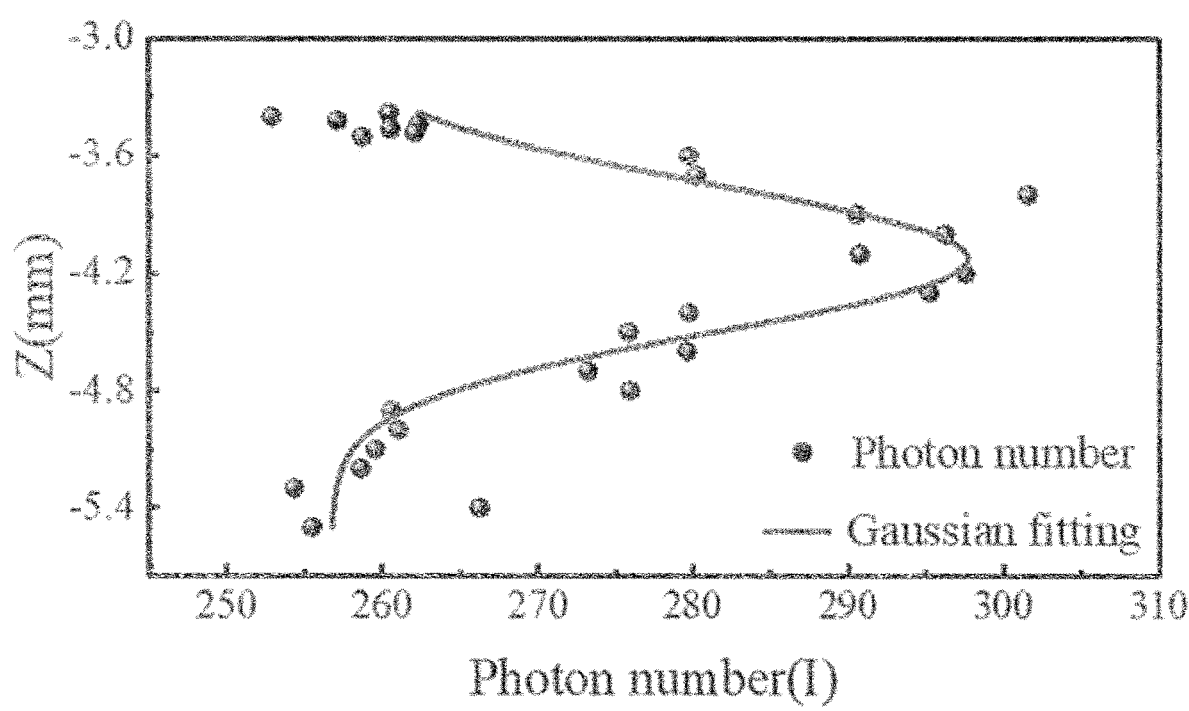
FIG. 8 is a distribution curve of a total light intensity in an illumination beam in the microlayer near an interface to z in an embodiment of the present invention.
Figure 9:
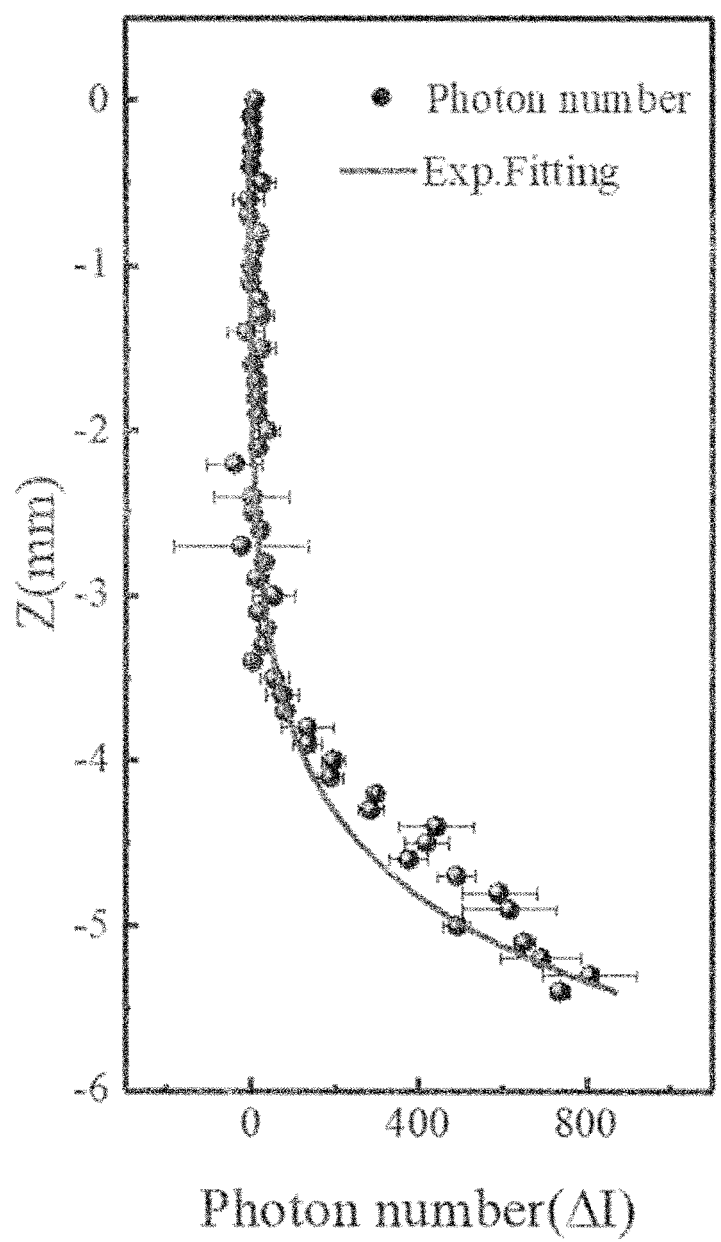
FIG. 9 is a distribution curve of a light intensity in a 100 μm layer obtained by means of a difference method to z in an embodiment of the present invention.

The fluorescence intensity (shown in FIG. 5 and FIG. 6) in the very thin optical layer can be precisely acquired by means the successive differential method.

TABLE 1

| | | | |
|---|---|---|---|
| $I_0$ | 10 | $Z_0$ | −0.21 mm |
| $I_1$ | 11 | $Z_1$ | −0.22 mm |
| $I_2$ | 12 | $Z_2$ | −0.32 mm |
| $I_3$ | 14 | $Z_3$ | −0.42 mm |
| $I_i$ | ... | $Z_i$ | ... |
| $I_{n-2}$ | 218 | $Z_{n-2}$ | −12.1 mm |
| $I_{n-1}$ | 224 | $Z_{n-1}$ | −12.6 mm |
| $I_n$ | 217 | $Z_n$ | −13.1 mm |

Of course, the invention is not limited to the above-mentioned implementation modes. Those skilled in the art could further make equivalent deformations or substitutions without violating the spirit of the present invention, and these equivalent deformations or substitutions are included in the scope defined by the claims of the disclosure.

What is claimed is:

1. A synchronous fluorescence detector for observing the interface concentration of fluorescent pollutants, comprising a first electric displacement platform, a quartz cuvette, an excitation light path, a collection light path and a second electric displacement platform, wherein the excitation light path comprises a high-power xenon lamp optical fiber light source, a short wavelength pass filter, an UV collimator, a first UV anti-reflection convex lens and a second UV anti-reflection convex lens; the collection light source comprises a third UV anti-reflection convex lens, a fourth UV anti-reflection convex lens, a long wavelength pass filter and a photomultiplier;

the excitation light path is arranged on the first electric displacement platform; the collection light path is arranged on the second electric displacement platform; the excitation light path and the collection light path are respectively close to the quartz cuvette; one side of the short wavelength pass filter is provided with the high-power xenon lamp optical fiber light source and another side of the short wavelength pass filter is provided with the UV collimator; another side of the UV collimator is provided with the first UV anti-reflection convex lens and the second UV anti-reflection convex lens;

in the excitation light path, divergent light emitted by the high-power xenon lamp optical fiber light source passes through the short wavelength pass filter and forms a divergent beam in a narrow wave band, the beam passes through the UV collimator to obtain an approximately parallel beam, the approximately parallel beam passes through the first UV anti-reflection convex lens and the second UV anti-reflection convex lens to form a thinner approximately parallel beam as incident light, and the incident light enters the quartz cuvette to excite a fluorescent pollutant to emit fluorescent light; and in the collection light path, a fluorescence signal emitted by the excited fluorescent pollutant passes through the third UV anti-reflection convex lens, the fourth UV anti-reflection convex lens and the long wavelength pass filter in sequence and is collected by the photomultiplier.

2. The synchronous fluorescence detector for observing the interface concentration of fluorescent pollutants according to claim 1, wherein in the excitation light path, a distance between the first UV anti-reflection convex lens and the second UV anti-reflection convex lens has to satisfy a corresponding relation between focal lengths of the two lenses.

3. The synchronous fluorescence detector for observing the interface concentration of fluorescent pollutants according to claim 1, wherein in the excitation light path, a lens combination formed by the first UV anti-reflection convex lens and the second UV anti-reflection convex lens are capable of being replaced by different types of UV collimators; and the excitation light path further comprises a columnar collecting lens in front of the UV collimator.

4. The synchronous fluorescence detector for observing the interface concentration of fluorescent pollutants according to claim 1, wherein each of the short wavelength pass filter and the long wavelength pass filter are capable of being replaced by a monochromator.

5. The synchronous fluorescence detector for observing the interface concentration of fluorescent pollutants according to claim 1, wherein in the collection light path, a lens combination formed by the third UV anti-reflection convex lens and the fourth UV anti-reflection convex lens are capable of being replaced by an UV objective lens with a greater NA value.

6. The synchronous fluorescence detector for observing the interface concentration of fluorescent pollutants according to claim 1, wherein an angle between the excitation light path and the collection light path are capable of being 0 degree, 90 degrees or 180 degrees.

7. The synchronous fluorescence detector for observing the interface concentration of fluorescent pollutants according to claim 1, wherein in the excitation light path, a distance between the second UV anti-reflection convex lens and the quartz cuvette is about 1-2 cm; and in the collection light path, a distance between the third UV anti-reflection convex lens and the quartz cuvette is about 1-2 cm.

8. The synchronous fluorescence detector for observing the interface concentration of fluorescent pollutants according to claim 1, wherein in the excitation light path, centers of the short wavelength pass filter, the UV collimator, the first UV anti-reflection convex lens and the second UV anti-reflection convex lens are on a same horizontal line; and in the collection light path, centers of the third UV anti-reflection convex lens, the fourth UV anti-reflection convex lens, the long wavelength pass filter and the photomultiplier are on a same horizontal line.

9. The synchronous fluorescence detector for observing the interface concentration of fluorescent pollutants according to claim 1, wherein a wavelength of the high-power xenon lamp optical fiber light source is as follows: 250 nm<$\lambda$<1000 nm; a filter range of the short wavelength pass filter is as follows: 300 nm<$\lambda$<350 nm; a ratio of the focal length of the first UV anti-reflection convex lens to that of the second UV anti-reflection convex lens is 1:4; a filter range of the long wavelength pass filter is as follows: 350 nm<$\lambda$<500 nm; a distance between the photomultiplier and the long wavelength pass filter is about 0.5-1 cm; and the minimum displacements of the first electric displacement platform and the second electric displacement platform moving longitudinally are 5 μm.

10. An application method of the synchronous fluorescence detector for observing the interface concentration of fluorescent pollutants according to claim 1, comprising the following specific steps:
   S1. turning on a power supply of the high-power xenon lamp optical fiber light source for preheating;
   S2. connecting communications between the first electric displacement platform and a computer and between the second displacement platform and the computer, and setting overload parameters to protect the displacement platforms;
   S3. connecting a communication between a counter of the photomultiplier and the computer, setting required parameters, and setting a single measurement time to be 2 s;
   S4. controlling the first electric displacement platform and the second displacement platform to move simultaneously by LabVIEW after preheating is completed, and acquiring data by using the photomultiplier, and repeating the step S4 in such a manner till an experiment is completed; and
   S5. processing the data acquired by the photomultiplier via a Python software and Excel.

11. An application method of the synchronous fluorescence detector for observing the interface concentration of fluorescent pollutants according to claim 2, comprising the following specific steps:
   S1. turning on a power supply of the high-power xenon lamp optical fiber light source for preheating;
   S2. connecting communications between the first electric displacement platform and a computer and between the second displacement platform and the computer, and setting overload parameters to protect the displacement platforms;
   S3. connecting a communication between a counter of the photomultiplier and the computer, setting required parameters, and setting a single measurement time to be 2 s;
   S4. controlling the first electric displacement platform and the second displacement platform to move simultaneously by LabVIEW after preheating is completed, and acquiring data by using the photomultiplier, and repeating the step S4 in such a manner till an experiment is completed; and
   S5. processing the data acquired by the photomultiplier via a Python software and Excel.

12. An application method of the synchronous fluorescence detector for observing the interface concentration of fluorescent pollutants according to claim 3, comprising the following specific steps:
   S1. turning on a power supply of the high-power xenon lamp optical fiber light source for preheating;
   S2. connecting communications between the first electric displacement platform and a computer and between the second displacement platform and the computer, and setting overload parameters to protect the displacement platforms;
   S3. connecting a communication between a counter of the photomultiplier and the computer, setting required parameters, and setting a single measurement time to be 2 s;
   S4. controlling the first electric displacement platform and the second displacement platform to move simultaneously by LabVIEW after preheating is completed, and acquiring data by using the photomultiplier, and repeating the step S4 in such a manner till an experiment is completed; and
   S5. processing the data acquired by the photomultiplier via a Python software and Excel.

13. An application method of the synchronous fluorescence detector for observing the interface concentration of fluorescent pollutants according to claim 4, comprising the following specific steps:
   S1. turning on a power supply of the high-power xenon lamp optical fiber light source for preheating;
   S2. connecting communications between the first electric displacement platform and a computer and between the second displacement platform and the computer, and setting overload parameters to protect the displacement platforms;
   S3. connecting a communication between a counter of the photomultiplier and the computer, setting required parameters, and setting a single measurement time to be 2 s;
   S4. controlling the first electric displacement platform and the second displacement platform to move simultaneously by LabVIEW after preheating is completed, and acquiring data by using the photomultiplier, and repeating the step S4 in such a manner till an experiment is completed; and
   S5. processing the data acquired by the photomultiplier via a Python software and Excel.

14. An application method of the synchronous fluorescence detector for observing the interface concentration of fluorescent pollutants according to claim 5, comprising the following specific steps:
   S1. turning on a power supply of the high-power xenon lamp optical fiber light source for preheating;
   S2. connecting communications between the first electric displacement platform and a computer and between the second displacement platform and the computer, and setting overload parameters to protect the displacement platforms;
   S3. connecting a communication between a counter of the photomultiplier and the computer, setting required parameters, and setting a single measurement time to be 2 s;
   S4. controlling the first electric displacement platform and the second displacement platform to move simultaneously by LabVIEW after preheating is completed, and acquiring data by using the photomultiplier, and repeating the step S4 in such a manner till an experiment is completed; and S5. processing the data acquired by the photomultiplier via a Python software and Excel.

15. An application method of the synchronous fluorescence detector for observing the interface concentration of fluorescent pollutants according to claim 6, comprising the following specific steps:
- S1. turning on a power supply of the high-power xenon lamp optical fiber light source for preheating;
- S2. connecting communications between the first electric displacement platform and a computer and between the second displacement platform and the computer, and setting overload parameters to protect the displacement platforms;
- S3. connecting a communication between a counter of the photomultiplier and the computer, setting required parameters, and setting a single measurement time to be 2 s;
- S4. controlling the first electric displacement platform and the second displacement platform to move simultaneously by LabVIEW after preheating is completed, and acquiring data by using the photomultiplier, and repeating the step S4 in such a manner till an experiment is completed; and
- S5. processing the data acquired by the photomultiplier via a Python software and Excel.

16. An application method of the synchronous fluorescence detector for observing the interface concentration of fluorescent pollutants according to claim 7, comprising the following specific steps:
- S1. turning on a power supply of the high-power xenon lamp optical fiber light source for preheating;
- S2. connecting communications between the first electric displacement platform and a computer and between the second displacement platform and the computer, and setting overload parameters to protect the displacement platforms;
- S3. connecting a communication between a counter of the photomultiplier and the computer, setting required parameters, and setting a single measurement time to be 2 s;
- S4. controlling the first electric displacement platform and the second displacement platform to move simultaneously by LabVIEW after preheating is completed, and acquiring data by using the photomultiplier, and repeating the step S4 in such a manner till an experiment is completed; and
- S5. processing the data acquired by the photomultiplier via a Python software and Excel.

17. An application method of the synchronous fluorescence detector for observing the interface concentration of fluorescent pollutants according to claim 8, comprising the following specific steps:
- S1. turning on a power supply of the high-power xenon lamp optical fiber light source for preheating;
- S2. connecting communications between the first electric displacement platform and a computer and between the second displacement platform and the computer, and setting overload parameters to protect the displacement platforms;
- S3. connecting a communication between a counter of the photomultiplier and the computer, setting required parameters, and setting a single measurement time to be 2 s;
- S4. controlling the first electric displacement platform and the second displacement platform to move simultaneously by LabVIEW after preheating is completed, and acquiring data by using the photomultiplier, and repeating the step S4 in such a manner till an experiment is completed; and
- S5. processing the data acquired by the photomultiplier via a Python software and Excel.

18. An application method of the synchronous fluorescence detector for observing the interface concentration of fluorescent pollutants according to claim 9, comprising the following specific steps:
- S1. turning on a power supply of the high-power xenon lamp optical fiber light source for preheating;
- S2. connecting communications between the first electric displacement platform and a computer and between the second displacement platform and the computer, and setting overload parameters to protect the displacement platforms;
- S3. connecting a communication between a counter of the photomultiplier and the computer, setting required parameters, and setting a single measurement time to be 2 s;
- S4. controlling the first electric displacement platform and the second displacement platform to move simultaneously by LabVIEW after preheating is completed, and acquiring data by using the photomultiplier, and repeating the step S4 in such a manner till an experiment is completed; and
- S5. processing the data acquired by the photomultiplier via a Python software and Excel.

* * * * *